United States Patent [19]

Payne

[11] Patent Number: 4,512,180

[45] Date of Patent: Apr. 23, 1985

[54] PELLET DURABILITY TESTER

[75] Inventor: John D. Payne, Whitchurch, England

[73] Assignee: Holmen Chemicals Limited, Hampshire, England

[21] Appl. No.: 460,014

[22] Filed: Jan. 21, 1983

[30] Foreign Application Priority Data

Jan. 28, 1982 [GB] United Kingdom ............... 8202417
Jun. 9, 1982 [GB] United Kingdom ............... 8216770

[51] Int. Cl.$^3$ ............................................. G01N 3/56
[52] U.S. Cl. ............................................. 73/7; 73/12; 73/78
[58] Field of Search ............ 73/12, 78, 432 V, 432 Z, 73/432 PS, 7, 86; 241/5, 39

[56] References Cited

U.S. PATENT DOCUMENTS

| | | | |
|---|---|---|---|
| 1,459,143 | 6/1923 | Curran | 73/12 X |
| 2,284,746 | 6/1942 | Kidwell | 241/39 |
| 2,644,328 | 7/1953 | Robinson et al. | 73/12 X |
| 3,184,952 | 5/1965 | Humphreys | 73/12 |
| 3,545,281 | 12/1970 | Johnston | 73/432 PS |
| 3,766,776 | 10/1973 | Williams | 73/12 X |
| 3,972,220 | 8/1976 | Moore | 73/7 |
| 4,109,507 | 8/1978 | Neidigh | 73/12 |
| 4,143,539 | 3/1979 | Baillie | 73/432 Z X |
| 4,179,916 | 12/1979 | Konnerth | 73/7 |

Primary Examiner—Charles A. Ruehl
Attorney, Agent, or Firm—Antonelli, Terry & Wands

[57] ABSTRACT

A pellet durability tester is provided which establishes the durability of manufactured pellets by subjecting them to circulation in a closed air re-circulation path and establishing the weight ratio of whole pellets in the sample before and after testing. The tester comprises a cabinet divided by an internal partion into two compartments, with one of these compartments constituting part of the re-circulation path. The pellets to be tested are introduced into the other compartment at its top and, in one embodiment, pass over a sieve to remove lose material from the whole pellets so that only the whole pellets are deposited into a container whose weight can be measured automatically. This container tips the pellet sample into the compartment for circulation around the re-circulation path. The re-circulation path also includes a swivel head which can direct the re-circulated air and material either into the compartment or back to the sieve so that the loose material is removed and the remaining whole pellets are received in the container for weighing. In a further embodiment, the tester at least partly dries the pellet sample prior to weighing by blowing air over it.

16 Claims, 7 Drawing Figures

PELLET DURABILITY TESTER

DESCRIPTION

The present invention relates to a pellet durability tester, in particular to an automated pellet durability tester for use on a production line in the manufacture of animal feed pellets.

Lignin chemical products are supplied to the animal feed industry where they are used as binders to improve physical quality of pelleted feedstuffs and also to improve efficiency of manufacture. The production of good physical quality pellets is very necessary in order to reduce wastage, maximize feed intake and improve efficiency of feed conversion.

Physical quality of pelleted feedstuffs is quantified by measuring "pellet durability" and one generally accepted method is by means of the "tumbling can" which tumbles 500 grammes of pellets for ten minutes, the weight of whole pellets remaining being expressed as a percentage of the initial weight. This method was devised by Professor Pfost of Kansas State University in the 1960's as a means of measuring the amount of pellet degradation which takes place during mechanical handling in the feed mill. However, it does not take account of degradation which takes place between mill and delivery to customer because in the 1960's the majority of feed was delivered in 25 kilo bags and therefore not subject to the rigours of bulk handling which today's pellets have to withstand. The advent of bulk transportation now means that the majority of pelleted feedstuffs is delivered by pressurized bulk tanker and blown into the farmer's store which in turn puts greater demands on the feed mill to produce tougher pellets. Unfortunately the feed mill did not have, at that time a means by which overall pellet degradation could be determined—the feed mill had no way of knowing beforehand what condition its pellets would be on reaching the customer's store.

In order to provide more meaningful information to the feed industry with respect to measurement of physical pellet quality the present inventor developed a tester which would stimulate the most rigorous treatment which pellets generally undergo, i.e. that of pneumatic handling. This tester circulated a 100 gramme sample of pellets in an airstream for two minutes during which time they negotiated a number of right angle bends and impinged repeatedly upon a hard surface before being deflected into a box at the base of the machine where whole pellets are separated from the meal particles.

The present invention provides an automated, pellet-durability tester comprising an air re-circulation path into which pellets may be introduced to determine their durability, means for introducing into the re-circulation path for testing a sample batch of pellets, means for removing the whole pellets remaining of the batch after testing and means for establishing the relative quantities of whole pellets in the sample before and after testing and thereby the durability of the pellets.

The means for establishing the durability of the pellets may be arranged to weigh the whole pellets before and after testing; for this purpose means may be provided for separating the whole pellets from any other material in the sample before and after testing. As far as the post-testing measurement is concerned, obviously weighing the whole pellets remaining is preferable to weighing the debris, i.e. broken pellets, meal, etc., although this could instead be weighed, and the weight subtracted from the original whole pellet weight providing any losses of material could be neglected.

In a convenient construction, the same separator may be used for separating the whole pellets from the other material before and after testing. For this purpose, the separator may be arranged in relation to an inlet of the tester from the production line with which it is to be used so that an incoming sample is separated and the whole pellets delivered to a collection point for introduction into the re-circulation path; a diverter may be provided which in one position constrains the sample to move in the re-circulation path and in a second position directs the sample towards the separator. The separator may, for example, be a mesh sieve or moving or gravity sieve.

For introduction into the re-circulation path, the whole pellets of the sample may be collected in a container which is moveable between a number of positions, namely a pellet-receiving position, a position in which it tips the pellets into the re-circulation path and, optionally a discharge position from which it discharges the pellets when they are finished with although as will be explained later this position may be the same as the second position. The discharge may be into a zone into which the remaining material separated from the whole pellets by the separator is also discharged and the material collected in this zone may be returned to the production line for re-processing. The pellet collecting container may be moveable between its three positions by rotation, preferably about a horizontal axis below the separator. The container may be supported by means of a load cell or other transducer producing a weight-related electrical signal so that the weight of the whole pellets before testing and those remaining after testing may be established.

In order to provide the re-circulation path, a square-"C" shaped length of tubing may be provided extending from a housing of the tester with the remaining run of the path defined within the cabinet. In order to establish the air-flow, preferably a blower provides a jet of air which exists into the part of the path within the cabinet via a nozzle so as to produce a negative pressure behind the nozzle to assist the circulation of the pellets. The re-circulation path may be arranged so that the momentum of the pellets causes them to collide with one or more hard surfaces so that weak pellets will break on impact.

The tester may be controlled by a computer used for controlling the operation of the pellet production line. This may be achieved broadly in one of two ways. Firstly the computer can control actuators within the tester for operating the diverter, sample container and so forth and also receives signals from the weight transducer to weigh the sample, the durability of the pellets being indicated by the relative weights of the whole pellets in the sample before and after testing. Alternatively, the tester may be an "intelligent" tester i.e. it may be provided with its own internal control circuitry which co-ordinates the operation of the actuators, handles analog to digital conversion of the pellet weights and communicates with the production line computer via a data link.

When a pellet tester is used in an on-line situation, it may be inconvenient to have to dry the pellets after pressing and prior to testing in the tester. Accordingly, a further aspect of this invention provides an on-line pellet tester which is provided with means for at least partially drying pellets straight from the pellet press prior to their introduction into the recirculating test path. Thus this aspect of the invention provides an automated pellet durability tester comprising a closed air recirculation path into which pellets may be introduced to determine their durability, means for holding the sample batch of pellets direct from a pellet press, means for at least partly drying and cooling pellets held in the holding means, means for introducing pellets once they are at least partly dried and cooled into the recirculation path for testing, means for removing the whole pellets remaining at the batch after testing and means for establishing the relative quantitities of whole pellets in the sample before and after testing and thereby the durability of the pellets.

Provided the conditions under which the batch are dried and cooled in the holding means are consistent from sample to sample, for a given plant it should be possible experimentally to determine a one-to-one relationship between the numerical results obtained which such partially dried and tested samples and sample batches with have been fully dried and cooled. The use of this aspect of the invention thus eliminates the need to cool and dry the pellets prior to their introduction into the tester.

A pellet tester according to the second aspect of the invention may have any or all of the various constructional and functional features described above in connection with the first aspect.

The invention will be further described by way of example with reference to the accompanying drawings in which.

Figure 1:
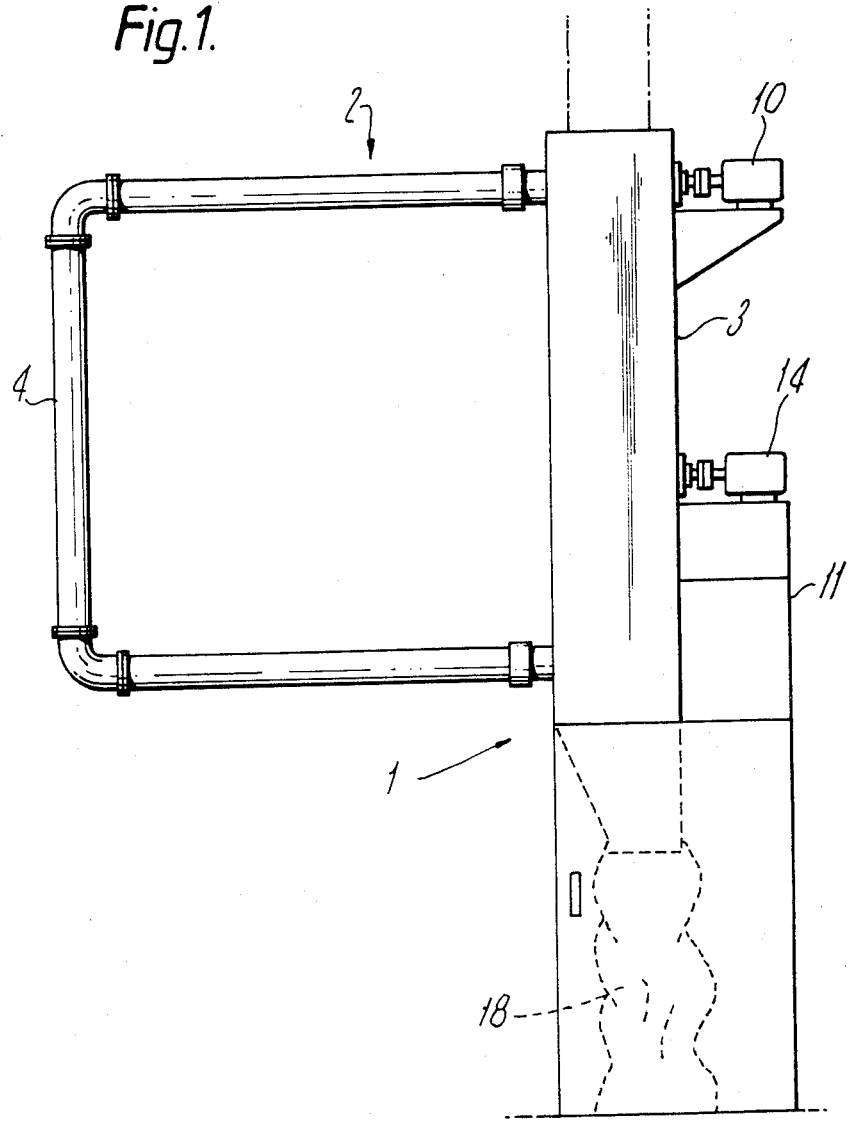
FIG. 1 is a side elevation of one embodiment of the present invention.

The pellet durability tester generally designated 1 in the figures has a closed re-circulation path 2 in a vertical plane in which pellets are re-circulated for a test period so that the degree to which the pellets are broken up, and thereby their durability, can be established. The re-circulation path is defined in part by an interior volume 6 of the main cabinet 3 of the tester, the remainder of the path being defined by a square "C" shaped piece of pipe work 4, preferably made of an electrically conductive material such as aluminum suitably earthed to prevent the build up of static in the re-circulation path. The interior volume in the cabinet forming the first part of the path may likewise be bounded by elements of an electrically conductive material.

The part of the re-circulation path within the cabinet 3 extends from a nozzle 5 through a volume 6 defined between the side wall 3a of the cabinet and a vertical partition 7 to a funnel 8 which discharges into an elbow 9 of the tube 4. The lower part of the partition 7 inclines towards the side wall 3a ending up at its lowest portion 7a parallel to it. The nozzle 5 can be swiveled by means of a drive motor 10 between the position shown in full lines in FIG. 2 which is used while pellets are being circulated around the re-circulation path to the position shown in chain dotted lines for a purpose to be described later.

The circulation of air and the pellets in the re-circulation path is achieved by means of a blower 11 which discharges air via a nozzle 12 into the corner of the elbow piece 9. As the air leaves the nozzle 12 it expands rapidly creating a negative pressure upstream in the re-circulation path thus causing more air and the pellets to be drawn into the pipe 4. The pressure head behind the nozzle 12 is converted into a velocity head in front of it and this action, known as the venturi principle, makes it possible to maintain a constant re-circulation of pellets in the air stream. Preferably the blower is arranged so that its windings, which get hot in operation, are outside and so do not heat the air being discharged through the nozzle 12. For this purpose the blower 11 may be of the axial flow type.

Figure 2:
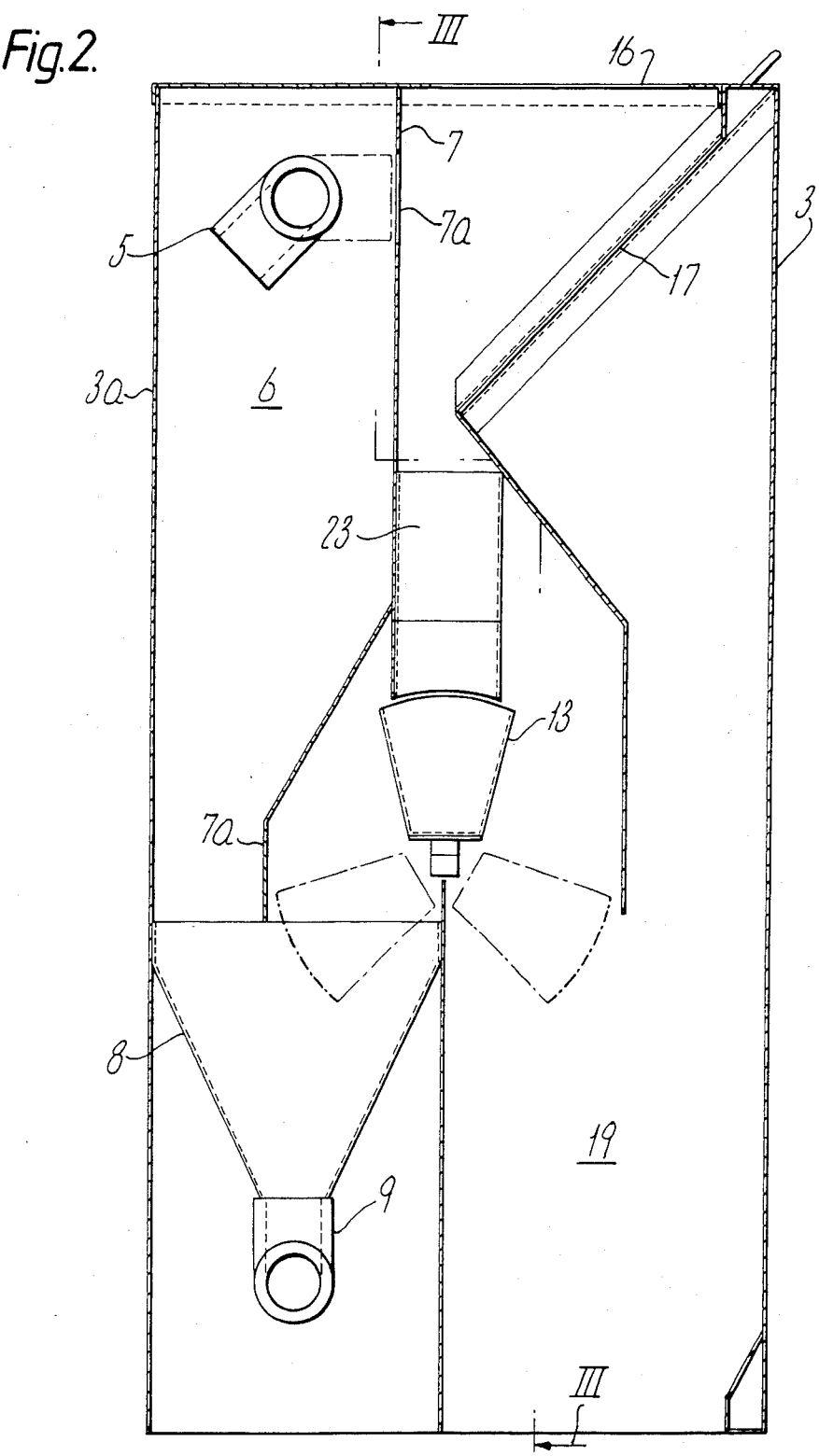
FIG. 2 is a vertical cross-section of the pellet tester of FIG. 1.
Figure 3:
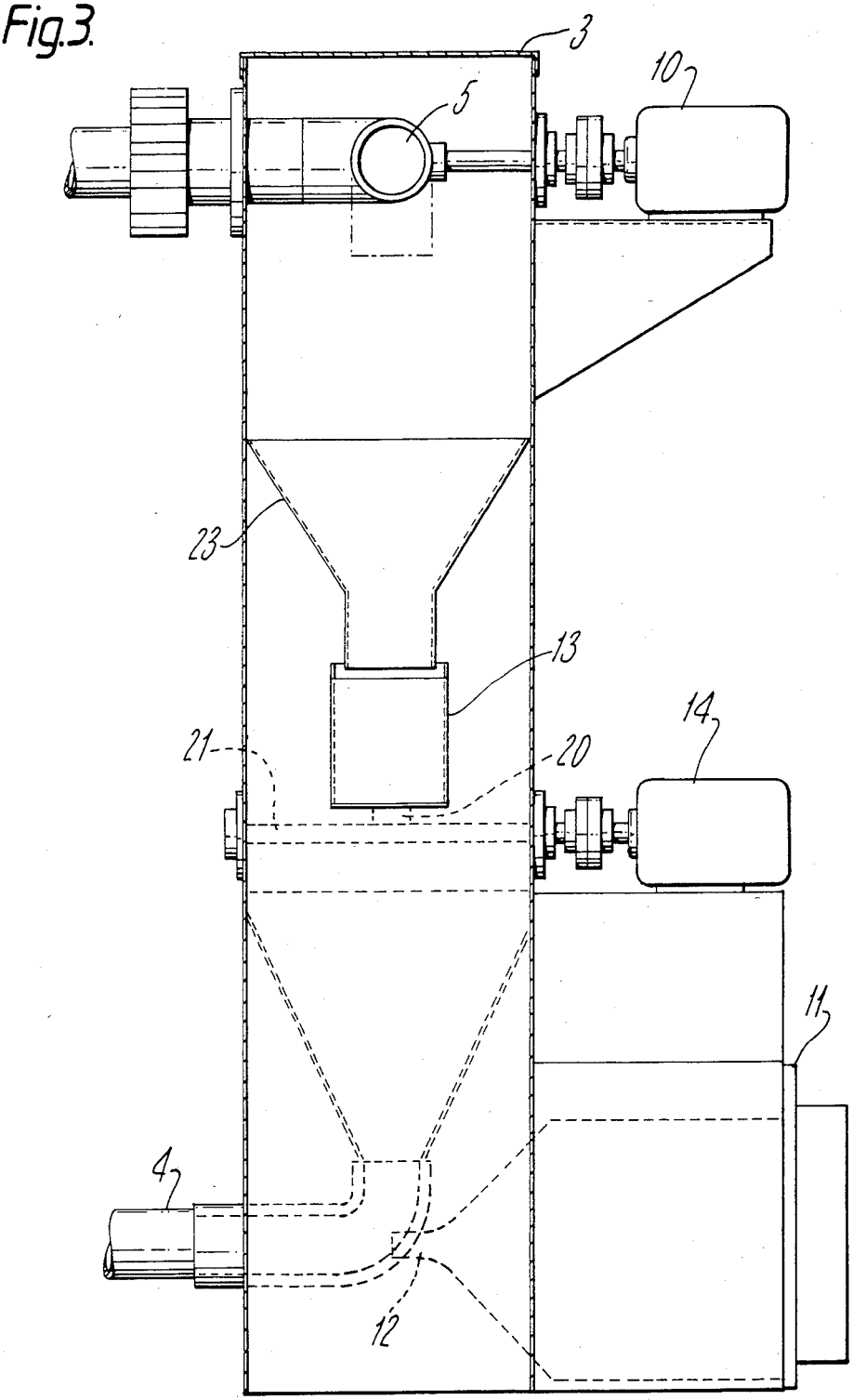
FIG. 3 is a section taken along line 3—3 in FIG. 2.

In order to introduce pellets to be tested into the re-circulation path, the tester 1 is provided with a collecting cup 13 which is rotatable by means of a drive motor 14 back and forth between the two chain dotted positions shown in FIG. 2. When in the position shown in full lines, the cup 13 may be loaded with a sample batch of whole pellets from the production line.

Figure 4:
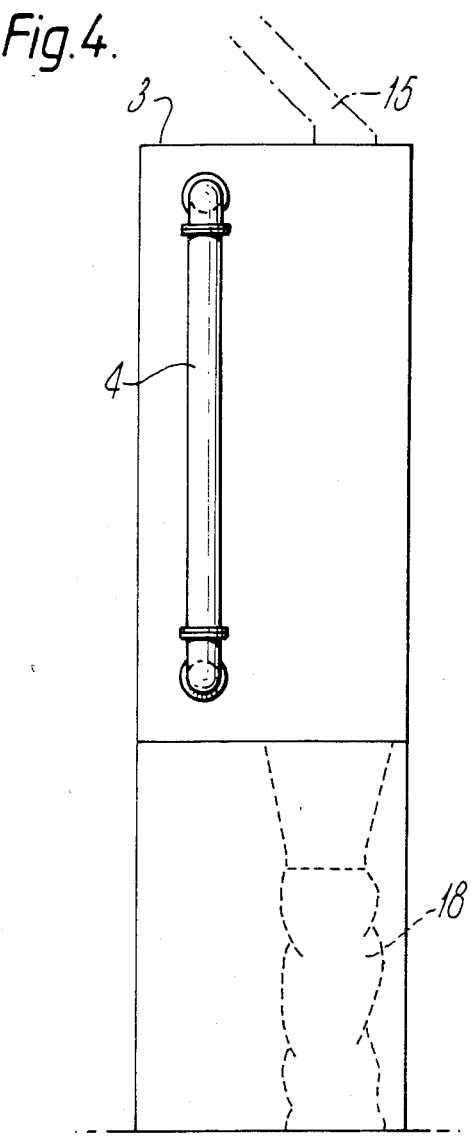
FIG. 4 is a front elevation of the tester of FIG. 1.
Figure 5:
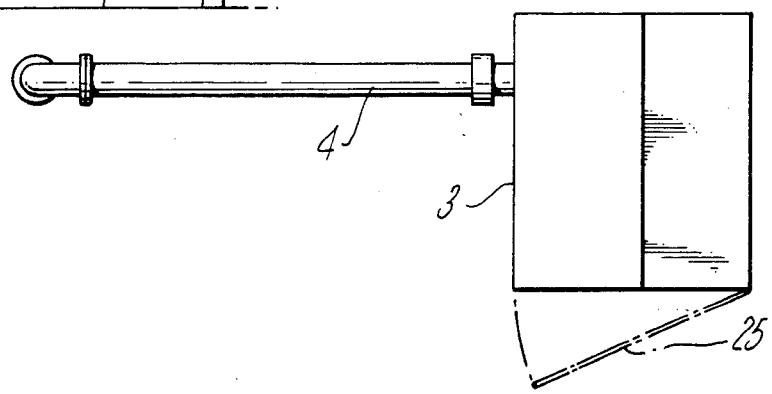
FIG. 5 is a plan view of the tester of FIG. 1.

In use, a sample batch of pellets are taken automatically by means of a specially designed volumetric metering device (not shown) fitted into a convenient pellet spout or cooler/sifter exit from the pellet press with which the tester 1 is being used. This batch of pellets is delivered via a chute 15 to an inlet 16 of the tester where it is discharged onto a gravity sifter screen 17 which allows only the whole pellets to reach the collecting cup 13; any broken pellets and other loose pellet material, etc., is discharged through the screen 17 into a collecting bag 18 (FIG. 4) within a collecting bin 19. The screen 17 is preferably removable for cleaning purposes and for replacement by others of different aperture sizes for different pellet diameters. Once the whole-pellet sample has had time to reach the collecting cup 13, the motor 14 is operated to rotate the cup 13 counterclockwise in FIG. 2 about its axis of rotation to the left hand chain dotted position to tip the pellets into the funnel 18 of the air re-circulation path. While circulating around the path 4 at least some of the pellets can be expected to be broken up in negotiating the right-angle bends and hitting the side walls of the volume 6. The precise sequence of operations will be described in more detail below. After passing around the re-circulation path for a given length of time, which may be varied for different pellet diameters, the motor 10 is operated to move the nozzle 5 to its chain dotted position in FIG. 2 so that pellets and other material as they exit the nozzle 5 are directed through an aperture 7a in the partition 7 towards the gravity screen 17 and the whole pellets are collected via a funnel 23 in the cup 13 (which has by now assumed its vertical position again) while the broken pellets and other pellet material are collected in the discharge bag 18 which can be removed via an access door 25 (FIG. 5). The weight of the whole pellets is then measured using the load cell 20 by means of which the collecting cup is supported on the shaft 21 driven by motor 14. Once the sample has been weighed and the weight noted, the motor 14 tips the cup 13 to its right-hand position to discharge the whole pellets into the collecting bag 18 for disposal. The contents of the bag 18 may be returned to the production line for processing. The tester may be modified so that all material entering the collecting bin 19 may be continuously returned to the production line.

Figure 6:
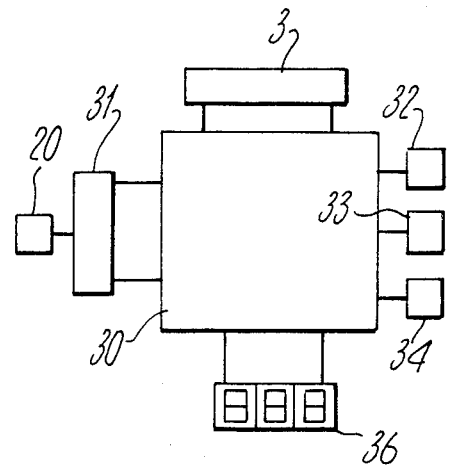
FIG. 6 is a somewhat schematic circuit diagram of the tester of FIGS. 1 to 5.

The tester 1 may be provided with a microprocessor based controller as indicated in FIG. 6. This controller comprises a microprocessor 30 programmed for the sequence of operations of the tester 1 and provided with temporary storage for storing the weight readings. The weight reading signals are derived from the load cell 20 at appropriate times via an analog to digital converter 31. Likewise the motors 10 and 14 and the motor of the blower 11 are controlled by drive circuits 32, 33 and 34 under the control of the microprocessor 30. The microprocessor 30 may also communicate with the computer operating the production line via an interface 35 by which means the computer may signal the tester 1 when it is about to receive a sample for testing and via which the pre- and post-testing whole pellet weights or their ratio as calculated by the microprocessor 30 optionally expressed as a percentage may be displayed by a display 36 and/or communicated back to the production line computer so that the results can be used e.g. for adjusting variables in the production process to maintain the durability of the pellets within desirable limits.

The testing of samples may take place regularly, for example once every 15 minutes per pellet press during production. Each test cycle will take, say, approximately three minutes therefore one tester may service four pellet presses. It is in these circumstances that the spent pellets, meal and dust be cycled automatically back from the collection bin to eliminate the need to empty the filter/collection bag 18. A signal from the computer controlling the pellet press or presses activates the appropriate sample in its sequence as and when that particular press is actually producing pellets. Alternatively, the cycle could be activated manually by the production controller.

In more detail, one possible scheme for the sequence of operation of the tester 1 for each test is as follows, this sequence taking place under control of the microprocessor 30:

1. On receipt of a signal from the production line computer, an auto sampling device will take a fixed volume of pellets from the feed mill system and deposit them into a spout which will deliver them via the chute 15 to the tester. The same initial signal will also activate the start of the tester's operation sequence. The whole pellets from the sample are directed by the screen 17 and funnel into the cup 13.

2. The weight of pellets in the cup 13 will be registered in the memory of the microprocessor 30 by a signal from the load cell 20 which carries the cup 13.

3. After the above signal has been accepted by the microprocessor 30 it will energize the motor of the blower 11. The movement of air in the tester will now tend to upset the stability of the cup 13 and the load cell therefore the microprocessor 30 will accept only the initial signal.

4. After a period of approximately 10 seconds, i.e. sufficient time for the air velocity in the tester 1 to stabilize, the load cell cup 13 will rotate thus depositing the pellets into the air stream. It will then return to its original position after a five second pause. The speed of rotation will be such that the pellets are not allowed to surge from the cup into the air stream which might otherwise cause a blockage.

5. For exactly two minutes, one minute or thirty seconds —according to pellet diameter—after the pellets have been tipped into the airstream, motor 10 will be operated; the elbow 5 will turn thus directing the pellets out of the airstream and back into the cup 13. Fines and broken pellets will be blown through the gravity screen and into the filter bag 18.

6. Approximately ten seconds after the elbow 5 has been activated the motor of the blower will be turned off.

7. Approximately ten seconds after stopping the fan motor the elbow 5 will return to its starting position.

8. After approximately ten more seconds the load cell 20 will signal the microprocessor 30 with the second weight result. On acceptance the microprocessor 30 then calculates the percentage by weight of whole pellets which remain, commits it to memory and/or displays the result on a visual display unit, and/or communicates the percentage to the production line computer.

9. On acceptance by the microprocessor 30 of the second weight signal the load cell cup assembly is rotated in the opposite direction to (4) thus depositing the spent pellets into the filter bag 18; a pause for approximately five seconds and it returns to its starting position whereupon the tester 1 is ready for the next cycle.

If required by the feed mill in which the tester is used, all durability results over a given period of production may be stored in the microprocessor 30's or the production line computer's memory and the microprocessor or computer programmed to provide a graphic display on a visual display unit as and when called for by the mill production operator. If the level of durability falls below an accepted level as set by the feed mill then the operator can call on the computer to provide information as to why pellet quality may be deteriorating.

Figure 7:
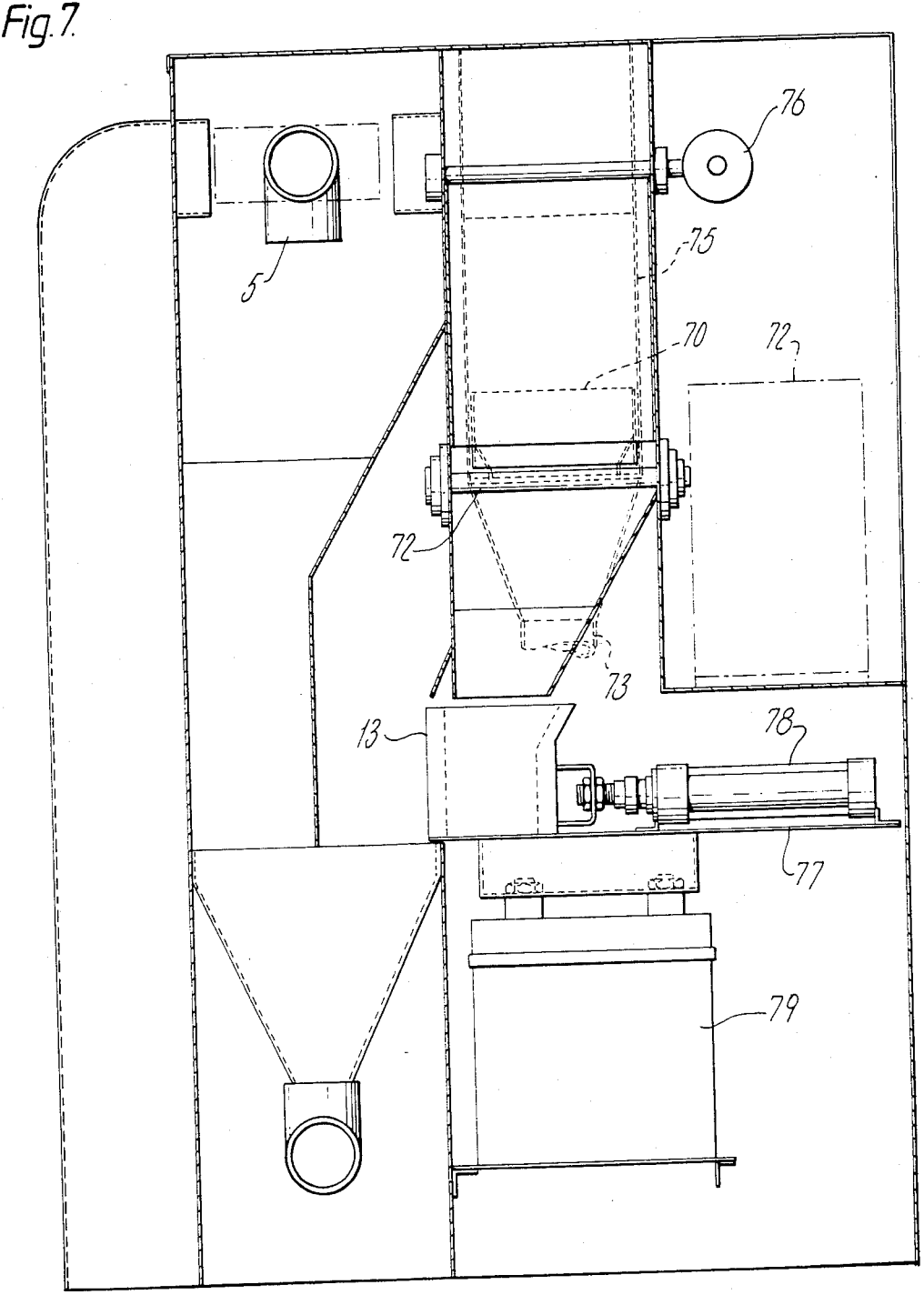
FIG. 7 is a view corresponding to FIG. 2 of an embodiment of the first and second aspects of the invention.

FIG. 7 is a view corresponding to FIG. 2 of a further form of a pellet tester embodying both apects of the present invention and for use in determining the durability characteristics of sample pellets direct from the pellet press of the plant, as described above. This embodiment is generally similar to that of FIGS. 1 to 6 so only the differences will be described here.

The screen 17 of the previous embodiment is replaced by a shallow, sieve-bottomed tray or box 70 which is mounted for pivoting about a shaft 17 driven by a drive motor and reduction gear 72 between the position shown in FIG. 7 in which it receives pellets direct from the pellet press via the access opening 16 to an counter-clockwise position where it can tip the pellets so collected into the cup 13. What happens is that during the operating cycle of the tester, once the pellets have been collected in the tray 70, the blower 11 (not shown in FIG. 7) sucks air via a duct 73 through the bottom of the tray 70 so as to partly cool and dry the pellets. During this part of the procedure, the nozzle 5 is directed as shown by the left hand chain dotted position in FIG. 7 so that any dust, fines and pellet fragments dislodged from the pellets in the tray 7 are directed down a vertical duct 74 to be discharged back to the pellet mill. Once the pellets in the tray 70 have been subjected to the air stream sucked through the blower 11 for a predetermined time, the air stream is cut off and the tray 70 pivoted to tip the pellets into the cup 13, in so doing pushing aside a flap 75 normally biased to a closed position by a counter-weight 76. From this stage, the sequence of operations is as for the embodiment of FIG. 1. For a particular plant it should be possible to obtain a one to one relation between results so obtained and those which would be obtained if the pellets were fully dried and cooled prior to testing.

Although the means for temporarily holding and partly drying and cooling the pellets has been exemplified by the tray 70 and duct 73 it will be appreciated that any other suitable arrangement for achieving the same effect may be used instead.

In the embodiment of FIG. 7, instead of being pivotally mounted, the cup 13 is open-bottomed and is slidable, leftwards from the position shown, on a plate 77, being driven by means of a linear air motor 78 also mounted on plate 77. At the appropriate stage in the operating cycle of the tester the motor 78 pushes the cup 13 leftwards to empty the pellets into the air recirculation path. Cup 13, plate 77 and motor 78 are mounted on a load cell 79 which is used to weigh the pellets. Once the pellets have been subjected to recirculation they are returned via nozzle 5 and tray 70 to the cup 13 for weighing. Once weighed they are tipped into the recirculation path again and are blown out of the tester via nozzle 5 (which has by then swivelled to its left hand position) and duct 74.

I claim:

1. A pellet durability tester comprising means for defining an air re-circulation path into which pellets may be introduced to determine their durability, means for introducing into the re-circulation path for testing a sample batch of pellets, means for removing the whole pellets remaining of the batch after testing and means for establishing the relative quantities of whole pellets in the sample before and after testing and thereby the durability of the pellets, and a diverter member movable between a first position in which it causes the batch material to continue re-circulating in the re-circulation path and a second position to deliver the material from the re-circulation path to the establishing means.

2. A tester according to claim 1, wherein the diverter member is hollow, its interior in part defining the re-circulation path when in said first position, and is mounted to swivel between the first and second positions.

3. A tester according to claim 2, wherein the diverter member is movable to a third position in which it discharges from the tester material in the re-circulation path.

4. A tester according to claim 1, wherein the diverter member is moveable to a third position in which it discharges from the tester material in the re-circulation path.

5. A tester according to claim 1, wherein the establishing means comprises a container for receiving the whole-pellet sample batch prior to circulation and material from the re-circulation path after circulation and means for measuring the weight of the container and material therein.

6. A tester according to claim 5, wherein the container is moveable between a first position in which it can receive the sample batch and a second position to introduce the batch into the re-circulation path.

7. A tester according to claim 1, further comprising sieve means arranged to sieve loose material from an incoming sample batch.

8. A tester according to claim 7, wherein the sieve means are arranged to sieve material received from the re-circulation path.

9. A tester according to claim 7, wherein the establishing means comprises a container for receiving the whole-pellet sample batch prior to circulation and material from the re-circulation path after circulation, and wherein a chute arrangement is provided for loading the container, the chute arrangement comprising the sieve means.

10. A tester according to claim 7, wherein the diverter member is arranged so as, in its second position, to deliver material to the sieve means.

11. A tester according to claim 1, and including drying means for at least partly drying the sample batch prior to its introduction into the re-circulation path.

12. A tester according to claim 11, wherein the drying means comprises means for holding the sample batch and means for directing a flow of air thereto.

13. A tester according to claim 12, further comprising a blower to produce the flow of air in the re-circulation path and said flow of air.

14. A tester according to claim 1, further including computing means for computing the ratio of the weights of whole pellets before and after testing in the re-circulation path.

15. A tester according to claim 14 wherein the computing means is programmed to control the operating sequence of the tester.

16. A pellet durability tester comprising a cabinet having first and second internal compartments, an air re-circulation path into which pellets may be introduced to determine their durability, the re-circulation path being constituted in part by the second compartment, a diverter member at the upper end of the second compartment for selectively directing air and material circulating in the re-circulation path into the first and second compartments, a container mounted for movement between a first position in which it receives test material introduced into the first compartment and a second position in which it tips pellets into the second compartment, means for weighing the container, means for separating remaining whole pellets from other material circulated in the re-circulation path and a blower for establishing the air-flow in the re-circulation path.

* * * * *